United States Patent [19]

Cormier et al.

[11] Patent Number: 5,451,407
[45] Date of Patent: Sep. 19, 1995

[54] REDUCTION OR PREVENTION OF SKIN IRRITATION OR SENSITIZATION DURING TRANSDERMAL ADMINISTRATION OF A IRRITATING OR SENSITIZING DRUG

[75] Inventors: Michel Cormier, Mountain View; Alfred Amkraut, Palo Alto, both of Calif.; Philip W. Ledger, Bedford, United Kingdom

[73] Assignee: ALZA Corporation, Palo Alto, Calif.

[21] Appl. No.: 63,176

[22] Filed: Jun. 21, 1993

[51] Int. Cl.⁶ ............................................. A61F 13/00
[52] U.S. Cl. .................................... 424/448; 424/449
[58] Field of Search ................................ 424/448, 449

[56] References Cited

U.S. PATENT DOCUMENTS

| | | | |
|---|---|---|---|
| 3,598,122 | 8/1971 | Zaffaroni | 424/20 |
| 3,598,123 | 8/1971 | Zaffaroni | 424/20 |
| 3,731,683 | 5/1973 | Zaffaroni | 128/268 |
| 3,797,494 | 3/1974 | Zaffaroni | 128/268 |
| 4,031,894 | 12/1978 | Smith | 424/361 |
| 4,046,886 | 12/1978 | Smith | 424/227 |
| 4,130,643 | 12/1978 | Smith | 424/238 |
| 4,130,667 | 12/1978 | Smith | 424/361 |
| 4,144,317 | 3/1979 | Higuchi | 424/21 |
| 4,201,211 | 5/1980 | Chandrasekaran et al. | 128/268 |
| 4,286,592 | 9/1981 | Chandrasekaran | 128/260 |
| 4,299,826 | 11/1981 | Luedders | 424/181 |
| 4,314,557 | 2/1982 | Chandrasekaran | 128/260 |
| 4,335,115 | 6/1982 | Thompson | 424/181 |
| 4,343,798 | 8/1982 | Fawzi | 424/240 |
| 4,379,454 | 4/1983 | Campbell et al. | 604/897 |
| 4,405,616 | 9/1983 | Rajadhyaksha | 424/244 |
| 4,435,180 | 3/1984 | Leeper | 604/896 |
| 4,559,222 | 12/1985 | Enscore et al. | 424/28 |
| 4,568,343 | 2/1986 | Leeper et al. | 604/896 |
| 4,573,995 | 3/1986 | Cheng et al. | 604/896 |
| 4,588,580 | 5/1986 | Gale et al. | 424/21 |
| 4,645,502 | 2/1987 | Gale et al. | 604/896 |
| 4,704,282 | 11/1987 | Campbell et al. | 424/449 |
| 4,746,515 | 5/1988 | Cheng et al. | 424/449 |
| 4,788,062 | 11/1988 | Gale et al. | 424/449 |
| 4,816,258 | 3/1989 | Nedberge et al. | 424/448 |
| 4,820,720 | 4/1989 | Sanders et al. | 514/356 |
| 4,834,076 | 5/1989 | Millet et al. | 128/65 |
| 4,840,790 | 6/1989 | Grollier et al. | 424/70 |
| 4,847,260 | 7/1989 | Abe et al. | 514/279 |
| 4,849,226 | 7/1989 | Gale | 424/448 |
| 4,863,738 | 9/1989 | Taskovich | 424/449 |
| 4,883,659 | 11/1989 | Goodman et al. | 424/74 |
| 4,885,154 | 12/1989 | Cormier et al. | 424/10 |

(List continued on next page.)

FOREIGN PATENT DOCUMENTS 0182635  5/1989  European Pat. Off.
2620330  3/1989  France.

OTHER PUBLICATIONS

J. of Pharmaceutical Sci., vol. 64, No. 4, Jun. 1975, Idson, Bernard, "Percutaneous Absorption" pp. 901–924.

Primary Examiner—D. Gabrielle Phelan
Attorney, Agent, or Firm—Michael J. Rafa; Steven F. Stone; Edward L. Mandell

[57] ABSTRACT

The present invention is directed to the transdermal administration of methyl nicotinate and an irritating or sensitizing drug. The invention includes a transdermal drug delivery device comprising a matrix adapted to be placed in irritating/sensitizing drug- and methyl nicotinate-transmitting relation with the skin site. The matrix contains sufficient amounts of irritating/sensitizing drug and of methyl nicotinate, in combination, to continuously administer to the skin for a predetermined period of time the drug to provide an effective therapeutic result. The invention is also directed to a method for either 1) preventing or reducing the irritation caused by an irritating drug or 2) preventing or reducing sensitization from occurring, as well as reducing or eliminating pain and discomfort occurring during the elicitation phase after sensitization has already been induced.

10 Claims, 6 Drawing Sheets

U.S. PATENT DOCUMENTS

| | | | |
|---|---|---|---|
| 4,895,727 | 1/1990 | Allen | 424/642 |
| 4,908,027 | 3/1990 | Enscore et al. | 604/890 |
| 4,940,586 | 7/1990 | Cheng et al. | 424/464 |
| 4,943,435 | 7/1990 | Baker et al. | 424/448 |
| 4,963,591 | 10/1990 | Fourman et al. | 514/944 |
| 4,968,685 | 11/1990 | Grollier | 514/256 |
| 4,973,474 | 11/1990 | Hocquaux et al. | 424/70 |
| 4,985,547 | 1/1991 | Yano et al. | 536/4.1 |
| 4,990,340 | 2/1991 | Hidala | 424/449 |
| 5,000,956 | 3/1991 | Amkraut | 424/434 |
| 5,004,610 | 4/1991 | Osborne et al. | 424/448 |
| 5,028,416 | 7/1991 | Yano et al. | 424/59 |
| 5,043,162 | 8/1991 | Trager | 424/401 |
| 5,049,387 | 9/1991 | Amkraut | 424/435 |
| 5,057,500 | 10/1991 | Thornfeldt | 514/53 |
| 5,071,971 | 12/1991 | Yano et al. | 536/4.1 |
| 5,077,054 | 12/1991 | Amkraut et al. | 424/486 |
| 5,100,672 | 3/1992 | Gueret et al. | 424/449 |
| 5,118,509 | 6/1992 | Amkraut | 424/449 |
| 5,120,545 | 6/1992 | Ledger et al. | 424/449 |
| 5,130,139 | 7/1992 | Cormier et al. | 424/450 |
| 5,132,106 | 7/1992 | Tuloup et al. | 424/70 |
| 5,145,675 | 9/1992 | Won | 424/78.31 |
| 5,151,271 | 9/1992 | Otsuka et al. | 424/443 |
| 5,156,601 | 10/1992 | Lorenz et al. | 604/307 |
| 5,171,576 | 12/1992 | Amkraut et al. | 424/449 |

REDUCTION OR PREVENTION OF SKIN IRRITATION OR SENSITIZATION DURING TRANSDERMAL ADMINISTRATION OF A IRRITATING OR SENSITIZING DRUG

FIELD OF THE INVENTION

This invention relates to the transdermal delivery of drugs. More particularly, this invention relates to the reduction or elimination of skin irritation or sensitization caused by the accumulation of irritating or sensitizing drugs.

BACKGROUND OF THE INVENTION

The transdermal route of parenteral drug delivery provides many advantages. Unfortunately, many drugs which are candidates for transdermal delivery have a tendency to cause skin irritation or sensitization, particularly when they are maintained in contact with the skin under occlusion for sustained periods of time. These drugs can cause undesirable skin reactions, such as itching and erythema. Therefore, despite the development of the transdermal drug delivery art, there remains a continuing need for an improved method of overcoming irritation or sensitization caused by transdermal delivery of an irritating/sensitizing drug.

Skin irritation can be caused by a variety of factors including, but not limited to, physical factors (e.g., chafing or occluding the skin in an airtight manner), exposure to certain chemicals, exposure to pH outside the normal range of the skin or mucosa, and bacterial overgrowth. Generally, tissue irritation is the manifested result of damage or toxicity to cells in the skin or mucosa caused by their response to a cytotoxic (i.e., irritating) agent.

Skin sensitization is a two-phase process involving distinct biological mechanisms of the human immune system. The first phase is called the induction phase. Induction occurs when the skin of an individual is first exposed to the sensitizing drug. Generally, no visible skin reaction is noted during the induction phase. Following induction, some of the individual's lymphocytes are specifically sensitized to the drug. The second phase of sensitization is called elicitation. Elicitation occurs when the individual is subsequently (i.e., after induction) exposed to the same sensitizing drug. Elicitation causes a skin reaction to occur. The skin reaction occurring during elicitation is known as contact dermatitis.

This invention is directed towards either 1) preventing or reducing the irritation caused by an irritating drug or 2) preventing or reducing sensitization from occurring, as well as reducing or eliminating pain and discomfort occurring during the elicitation phase after sensitization has already been induced.

SUMMARY OF THE INVENTION

According to the present invention, it has been discovered that methyl nicotinate may be safely and efficaciously administered transdermally, together with a irritating or sensitizing drug, to reduce or prevent skin irritation or sensitization. The invention includes a transdermal drug delivery device containing sufficient amounts of methyl nicotinate and of irritating/sensitizing drug, in is combination, to provide administration of the irritating/sensitizing drug through the skin for a predetermined period of time, while reducing or preventing skin irritation or sensitization.

The invention is also directed to a method for the transdermal administration of methyl nicotinate and an irritating or sensitizing drug, in combination, to reduce or prevent skin irritation or sensitization.

DETAILED DESCRIPTION OF THE INVENTION AND PREFERRED EMBODIMENTS

Figure 1:
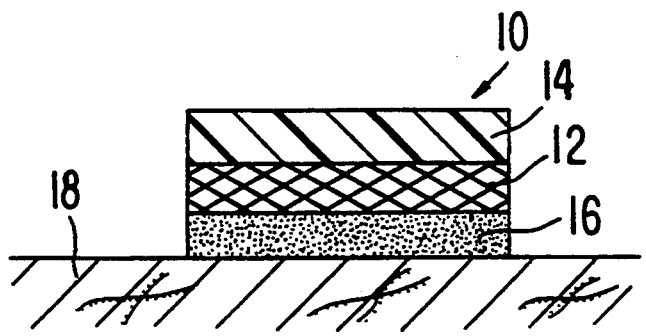
FIG. 1 is a cross-section through a schematic perspective view of one embodiment of transdermal therapeutic devices according to this invention.

According to the present invention, it has been found that an irritating or sensitizing drug can be administered to the human body in a therapeutically effective amount via the transdermal route when it is co-administered with methyl nicotinate.

Typical transdermal delivery devices are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,573,995; 4,588,580; 4,645,502; 4,704,282; 4,788,062; 4,816,258; 4,849,226; 4,908,027; 4,943,435; and 5,004,610. The disclosures of the above patents are incorporated herein by reference. The co-administration of an irritating or sensitizing drug and methyl nicotinate as disclosed herein can be accomplished by using transdermal devices of these kinds.

The present invention is applicable to any drug which is normally delivered through the skin or mucosa, and which tends to cause irritation or sensitization following transdermal application of the drug to the skin or mucosa. As used herein, the term "drug" is intended to have its broadest interpretation as any biologically active substance which is delivered to a living organism to produce a desired, usually beneficial, effect. In general, this includes beneficial agents in all of the major therapeutic areas including, but not limited to: ACE inhibitors, adenohypophyseal hormones, adrenergic neuron blocking agents, adrenocortical steroids, inhibitors of the biosynthesis of adrenocortical steroids, alpha-adrenergic agonists, alpha-adrenergic antagonists, selective alphas two-adrenergic agonists, analgesics, antipyretics and anti-inflammatory agents, androgens, local anesthetics, general anesthetics, antiaddictive agents, antiandrogens, antiarrhythmic agents, antiasthmatic agents, anticholinergic agents, anticholinesterase agents, anticoagulants, antidiabetic agents, antidiarrheal agents, antidiuretic, antiemetic and prokinetic agents, antiepileptic agents, antiestrogens, antifungal agents, antihypertensive agents, antimicrobial agents, antimigraine agents, antimuscarinic agents, antineoplastic agents, antiparasitic agents, antiparkinson's agents, antiplatelet agents, antiprogestins, antithyroid agents, antitussives, antiviral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, catecholamines and sympathomimetic drugs, cholinergic agonists, cholinesterase reactivators, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, 5-hydroxytryptamine antagonists, drugs for the treatment of hyperlipoproteinemia, hypnotics and sedatives, immunosuppressive agents, laxatives, methylxanthines, monoamine oxidase inhibitors, neuromuscular blocking agents, organic nitrates, opioid analgesics and antagonists, pancreatic enzymes, phenothiazines, progestins, prostaglandins, agents for the treatment of psychiatric disorders, retinoids, sodium channel blockers, agents for spasticity and acute muscle spasms, succinimides, thioxanthenes, thrombolytic agents, thyroid agents, tricyclic antidepressants, inhibitors of tubular transport of organic compounds, drugs affecting uterine motility, vasodilators, vitamins and the like.

Representative irritating or sensitizing drugs within these classes include by way of example and not for purposes of limitation, alprenolol, aminopromazine, amitriptyline, antazoline, atropine, azatadine, buprenorphine, buspirone, chloroquine, chlorpheniramine, chlorpromazine, chlorprothixene, clemastine, clomipramine, clonidine, cyclobenzaprine, cyproheptadine, deprenyl, desipramine, dexchlorpheniramine, dexsecoverine, dibucaine, diclofenac, digitoxin, digoxin, diphenylpyraline, dothiepin, doxepin, enalapril, ethacrynic acid, ethopropazine, fluphenazine, hydromorphone, imipramine, indomethacin, ketoprofen, ketorolac, levorphanol, methadone, methdilazine, nalbuphine, naloxone, naltrexone, nortriptyline, ondansetron, oxybutynin, perphenazine, phenelzine, phenylpropylamine, prochlorperazine, promazine, promethazine, propiomazine, propionylpromazine, propranolol, protriptyline, secoverine, tetracaine, timolol, tranylcypromine, trifluoperazine, triflupromazine, trimeprazine, trimipramine, triprolidine, verapamil, and the like.

Because of the wide variation in skin permeability from individual and from site to site on the same body, it may be preferable that an irritating drug and methyl nicotinate be administered from a rate-controlled transdermal delivery device. Rate control can be obtained either through a rate-controlling membrane or adhesive or through the other means disclosed in the patents noted above.

A certain amount of irritating drug will bind to the skin, and it is accordingly preferred that the skin-contacting layer of the device include this amount of the drug as a loading dose.

Figure 2:
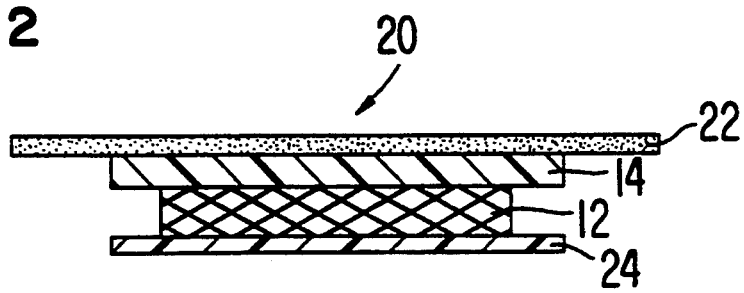
FIG. 2 is a cross-section through another embodiment of a transdermal therapeutic device according to this invention.
Figure 3:
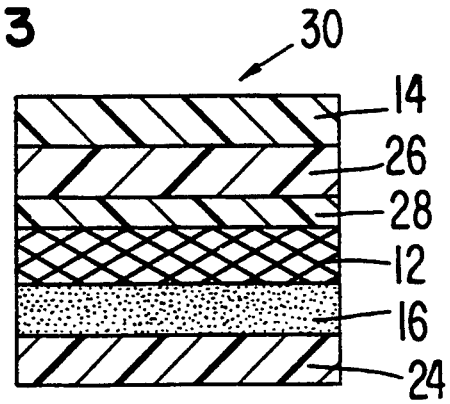
FIG. 3 is a cross-section through another embodiment of a transdermal therapeutic device according to this invention.

Examples of suitable transdermal delivery devices are illustrated in FIGS. 1, 2 and 3. In the drawings, the same reference numbers are used throughout the different figures to designate the same or similar components. The figures are not drawn to scale.

In FIG. 1, transdermal delivery device 10 comprises a reservoir 12 containing both the irritating/sensitizing drug and methyl nicotinate. Reservoir 12 is preferably in the form of a matrix containing the irritating/sensitizing drug and methyl nicotinate dispersed therein. Reservoir 12 is sandwiched between a backing layer 14 and an in-line contact adhesive layer 16. The device 10 adheres to the surface of the skin 18 by means of the adhesive layer 16. The adhesive layer 16 may optionally contain the irritating/sensitizing drug and/or methyl nicotinate. A strippable release liner (not shown in FIG. 1) is normally provided along the exposed surface of adhesive layer 16 and is removed prior to application of device 10 to the skin 18. Optionally, a rate-controlling membrane (not shown) may be present between the reservoir 12 and the adhesive layer 16.

Alternatively, as shown in FIG. 2, transdermal therapeutic device 20 may be attached to the skin or mucosa of a patient by means of an adhesive overlay 22. Device 20 is comprised of an irritating/sensitizing drug and methyl nicotinate-containing reservoir 12 which is preferably in the form of a matrix containing irritating/sensitizing drug and methyl nicotinate dispersed therein. A backing layer 14 is provided adjacent one surface of reservoir 12. Adhesive overlay 22 maintains the device on the skin and may be fabricated together with, or provided separately from, the remaining elements of the device. With certain formulations, the adhesive overlay 22 may be preferable to the in-line contact adhesive 16 as shown in FIG. 1. This is true, for example, where the is irritating/sensitizing drug and methyl nicotinate reservoir contains a material which adversely affects the adhesive properties of the in-line contact adhesive layer 16. Backing layer 14 is preferably slightly larger than reservoir 12, and in this manner prevents the materials in reservoir 12 from adversely interacting with the adhesive in overlay 22. Optionally, a rate-controlling membrane (not shown in FIG. 2) may be provided on the skin-proximal side of reservoir 12. A strippable release liner 24 is also provided with device 20 and is removed just prior to application of device 20 to the skin.

In FIG. 3, transdermal delivery device 30 comprises an irritating/sensitizing drug and methyl nicotinate containing reservoir 12 substantially as described with respect to FIG. 1. Permeation enhancer reservoir ("enhancer reservoir") 26 comprises permeation enhancer dispersed throughout and is substantially free of any undissolved irritating/sensitizing drug. Enhancer reservoir 26 is preferably made from substantially the same matrix as is used to form drug reservoir 12. A rate-controlling membrane 28 for controlling the release rate of the permeation enhancer from enhancer reservoir 26 to drug reservoir 12 is placed between the two reservoirs. A rate-controlling membrane (not shown in FIG. 3) for controlling the release rate of the enhancer from drug reservoir 12 to the skin may also optionally be utilized and would be present between adhesive layer 16 and reservoir 12.

The rate-controlling membrane may be fabricated from permeable, semipermeable or microporous materials which are known in the art to control the rate of agents into and out of delivery devices and having a permeability to the permeation enhancer lower than that of drug reservoir 12. Suitable materials include, but are not limited to, polyethylene, polyvinyl acetate and ethylene vinyl acetate copolymers.

Superimposed over the permeation enhancer reservoir 26 of device 30 is a backing 14. On the skin-proximal side of reservoir 12 are an adhesive layer 16 and a strippable liner 24 which would be removed prior to application of the device 30 to the skin.

In the embodiments of FIGS. 1, 2 and 3, the carrier or matrix material of the reservoirs has sufficient viscosity to maintain its is shape without oozing or flowing. If, however, the matrix or carrier is a low viscosity flowable material such as a liquid or a gel, the composition can be fully enclosed in a pouch or pocket, as known to the art from U.S. Pat. No. 4,379,454 (noted above), for example, and as illustrated in FIG. 4.

Figure 4:
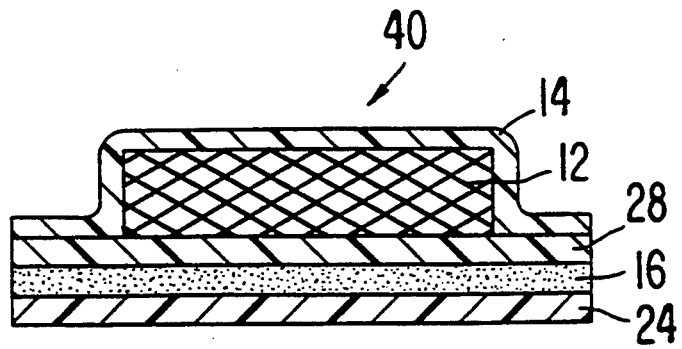
FIG. 4 is a cross-section through yet another embodiment of a transdermal therapeutic device according to this invention.

Device 40 shown in FIG. 4 comprises a backing member 14 which serves as a protective cover for the device, imparts structural support, and substantially keeps components in device 40 from escaping the device. Device 40 also includes reservoir 12 which contains the irritating/sensitizing drug and methyl nicotinate and bears on its surface distant from backing member 14 a rate-controlling membrane 28 for controlling the release of the irritating/sensitizing drug and/or methyl nicotinate from device 40. The outer edges of backing member 14 overlay the edges of reservoir 12 and are joined along the perimeter with the outer edges of the rate-controlling membrane 28 in a fluid-tight arrangement. This sealed reservoir may be effected by pressure, fusion, adhesion, an adhesive applied to the edges, or other methods known in the art. In this manner, reservoir 12 is contained wholly between backing member 14 and rate-controlling membrane 28. On the skin-proximal side of rate-controlling membrane 28 are an adhesive layer 16 and a strippable liner 24 which would be removed prior to application of the device 40 to the skin.

In an alternative embodiment of device 40 of FIG. 4, reservoir 12 contains a permeation enhancer only and is substantially free of irritating/sensitizing drug. The irritating/sensitizing drug and methyl nicotinate are present in adhesive layer 16 which acts as a separate reservoir.

The irritating/sensitizing drug and methyl nicotinate can be co-extensively administered to human skin or mucosa from a skin patch or other known transdermal delivery device which contains a saturated or unsaturated formulation of an irritating/sensitizing drug and methyl nicotinate.

The formulation may be aqueous or non-aqueous based. The formulation should be designed to deliver the irritating/sensitizing drug and methyl nicotinate at the necessary release rates. Aqueous formulations typically comprise water or water/ethanol and about 1–2 wt % of a gelling agent, an example being a hydrophilic polymer such as hydroxyethylcellulose or hydroxypropylcellulose. Typical non-aqueous gels are comprised of silicone fluid or mineral oil. Mineral oil-based gels also typically contain 1–2 wt % of a gelling agent such as colloidal silicon dioxide. The suitability of a particular gel depends upon the compatibility of its constituents with both the irritating/sensitizing drug and the methyl nicotinate and any other components in the formulation.

The reservoir matrix should be compatible with the irritating/sensitizing drug, the methyl nicotinate, a permeation enhancer, if present, and any carrier therefor. The term "matrix" as used herein refers to a well-mixed composite of ingredients fixed into shape. When using an aqueous-based formulation, the reservoir matrix is preferably a hydrophilic polymer, e.g., a hydrogel. When using a non-aqueous-based formulation, the reservoir matrix is preferably composed of a hydrophobic polymer. Suitable polymeric matrices are well known in the transdermal drug delivery art, and examples are listed in the above-named patents previously incorporated herein by reference.

A typical laminated system would comprise a polymeric membrane and/or matrix such as ethylene vinyl acetate (EVA) copolymers, such as those described in U.S. Pat. No. 4,144,317, preferably having a vinyl acetate (VA) content in the range of from about 9% up to about 60% and more preferably about 28% to about 60% VA. Polyisobutylene/oil polymers containing from 4–25% high molecular weight polyisobutylene and 20–81% low molecular weight polyisobutylene with the balance being an oil such as mineral oil or polybutynes may also be used as the matrix material.

The aforementioned patents describe a wide variety of materials which can be used for fabricating the various layers or components of the transdermal delivery devices according to this invention. This invention therefore contemplates the use of materials other than those specifically disclosed herein, including those which may hereafter become known to the art to be capable of performing the necessary functions.

The amount of irritating/sensitizing drug present in the therapeutic device and required to achieve an effective therapeutic result depends on many factors, such as the minimum necessary dosage of drug for the particular indication being treated; the solubility and permeability of the matrix, of the adhesive layer and of the rate-controlling membrane, if present; and the period of time for which the device will be fixed to the skin. The minimum amount of drug is determined by the requirement that sufficient quantities of drug must be present in the device to maintain the desired rate of release over the given period of application. The maximum amount for safety purposes is determined by the requirement that the quantity of drug present cannot exceed a rate of release that reaches toxic levels.

When a constant irritating/sensitizing drug delivery rate is desired, the drug is normally present in the matrix or carrier at a concentration in excess of saturation, the amount of excess being a function of the desired length of the drug delivery period of the system. The drug may, however, be present at a level below saturation without departing from this invention as long as the drug is continuously administered to the same skin or mucosa site in an amount and for a period of time sufficient to provide the desired therapeutic rate and delivery profile of drug delivery.

Optionally, permeation enhancer(s) is dispersed through the matrix or carrier, preferably at a concentration sufficient to provide permeation-enhancing amounts of enhancer in the reservoir throughout the anticipated administration period. Where there is an additional, separate permeation enhancer matrix layer as well, as in FIGS. 3 and 4, the permeation enhancer normally is present in the separate reservoir in excess of saturation.

The use of permeation enhancers for transdermal administration is described in numerous technical publications and patents, such as U.S. Pat. Nos. 4,940,586;

4,863,738; 4,820,720; 4,746,515; 4,568,343; 4,405,616; 4,379,454; 4,343,798; 4,335,115; 4,299,826; 4,130,667; 4,130,643; 4,046,886; British Patent No. 1,001,949 and Idson, Percutaneous Absorption, *J. Phar. Sci.*, Vol. 64, No. 66, June 1975, pp. 901–924, which are incorporated herein by reference.

In addition to the irritating/sensitizing drug, the methyl nicotinate and a suitable permeation enhancer, which are essential to the invention, the matrix or carrier may also contain dyes, pigments, inert fillers, excipients and other conventional components of pharmaceutical products or transdermal devices known to the art.

In the present invention, the irritating/sensitizing drug is delivered at a therapeutically effective rate (that is, a rate that provides a desired therapeutic effect) and the methyl nicotinate is delivered at a preventing or reducing irritating/sensitizing rate (that is, a rate that provides decreased irritation/sensitization of the irritating/sensitizing drug) for a predetermined time period and in the required delivery pattern.

A preferred embodiment of the present invention comprises a method for the transdermal administration of 0.005 to 10.0 percent weight per volume (herein after "w/v") methyl nicotinate in combination with a therapeutic effective amount an irritating or sensitizing drug, to reduce or prevent skin irritation or sensitization.

A more preferred embodiment of the present invention comprises a method for the transdermal administration of 0.5 to 5.0 percent w/v methyl nicotinate in combination with a therapeutic effective amount an irritating or sensitizing drug, to reduce or prevent skin irritation or sensitization.

The administration rate of the drug through the skin should be sufficient to minimize the size of the device. The size of the device of this invention can vary from less than 1 cm$^2$ to greater than 200 cm$^2$. A typical device, however, will have a size within the range of 5–50 cm$^2$. The delivery device containing the irritating/sensitizing drug and the methyl nicotinate is placed on a user such that the device is delivering the irritating/sensitizing drug in a therapeutically effective amount to the user.

The length of time of irritating/sensitizing drug presence and the total amount of irritating/sensitizing drug in the plasma can be changed following the teachings of this invention to provide different treatment regimens. Thus, they can be controlled by the amount of time during which exogenous drug is delivered transdermally to an individual or animal.

The devices of this invention can be designed to effectively deliver irritating/sensitizing drug for an extended time period of from several hours up to 7 days or longer. Seven days is generally the maximum time limit for application of a single device because the adverse affect of occlusion of a skin site increases with time and the normal cycle of slodding and replacement of the skin cells occurs in about 7 days. The transdermal therapeutic devices of the present invention are prepared in a manner known in the art, such as by those procedures, for example, described in the transdermal device patents listed previously herein. Having thus generally described the invention, the following specific examples describe preferred embodiments thereof.

DETAILED DESCRIPTION OF EXAMPLES

EXAMPLE 1

The following formulations were made to determine the effect of methyl nicotinate on chloroquine-induced irritation:

1) chloroquine base 1% w/v, ethanol 24% w/v, HEPPS 5% w/v, hydroxyethylcellulose gel 2% w/v, NaOH q.s. pH 8.5 and distilled water q.s.,
2) chloroquine base 1% w/v, methyl nicotinate 0.05 w/v, ethanol 24% w/v, HEPPS 5% w/v, hydroxyethylcellulose gel 2% w/v, NaOH q.s. pH 8.5 and distilled water q.s.,
3) methyl nicotinate 0.05 w/v, ethanol 24% w/v, HEPPS 5% w/v, hydroxyethyl cellulose gel 2% w/v, NaOH q.s. pH 8.5 and distilled water q.s., and
4) ethanol 24% w/v, HEPPS 5% w/v, hydroxyethylcellulose gel 2% w/v, NaOH q.s. pH 8.5 and distilled water q.s.

0.020 ml of each formulation was placed in a Finn ® chamber. The chambers were inverted and applied to four skin sites on the forearm of an adult human male. After 16 hours the cups were removed and the sites were washed. At 3 hours, 8 hours, 1 day, 2 days, 3 days, 4 days, 6 days and 7 days thereafter, the sites were observed and the intensity of the irritant reaction was scored with a Minolta ® Chroma Meter.

Figure 5:
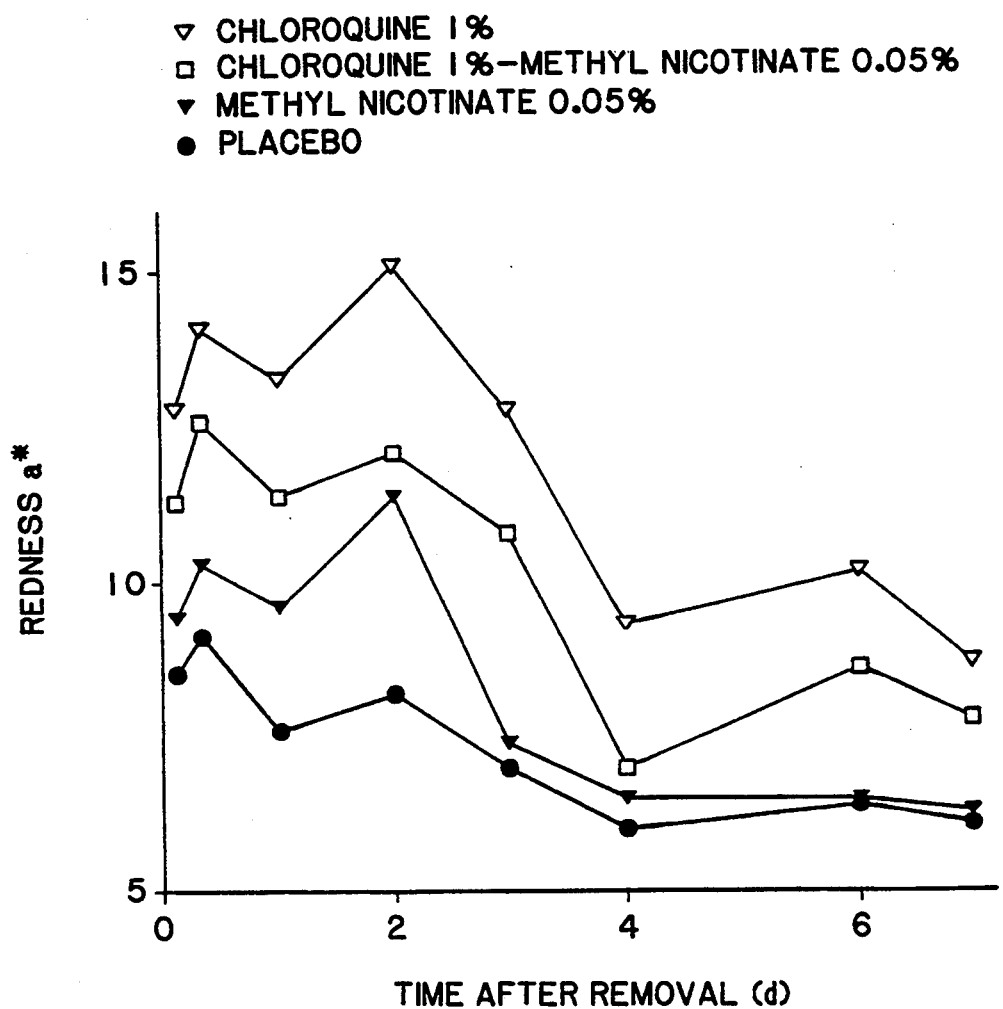
FIG. 5 is a graph showing the effect of methyl nicotinate on chloroquine-induced irritation.

The Minolta ® Chroma Meter converts all colors within the range of human perception into a numerical code using the L*, a* and b* notation system. L* expresses brightness on the black-white axis; a* expresses hue on the red-green axis; and b* expresses chroma on the yellow-blue axis so that a specific numerical code enables an exact color description of an object. Minolta ® measurements were made by taking the mean a* value of three readings at the treated site. That result was then subtracted from the mean a* value of three readings at adjacent sites treated with a placebo formulation. As can be seen in FIG. 5, it was found that the methyl nicotinate reduced the irritant reaction.

EXAMPLE 2

The following formulations were made to determine the effect of methyl nicotinate on the elicitation of sensitization to propranolol:

1) 0.1 w/v percent propranolol base, 32 w/v percent ethanol, 5 w/v percent HEPPS, 2 w/v percent hydroxyethylcellulose, NaOH q.s. pH 8 and distilled water q.s., and
2) 0.1 w/v percent propranolol base, 0.05 w/v percent methyl nicotinate, 32 w/v percent ethanol, 5 w/v percent HEPPS, 2 w/v percent hydroxyethylcellulose, NaOH q.s. pH 8 and distilled water q.s.

Figure 6:
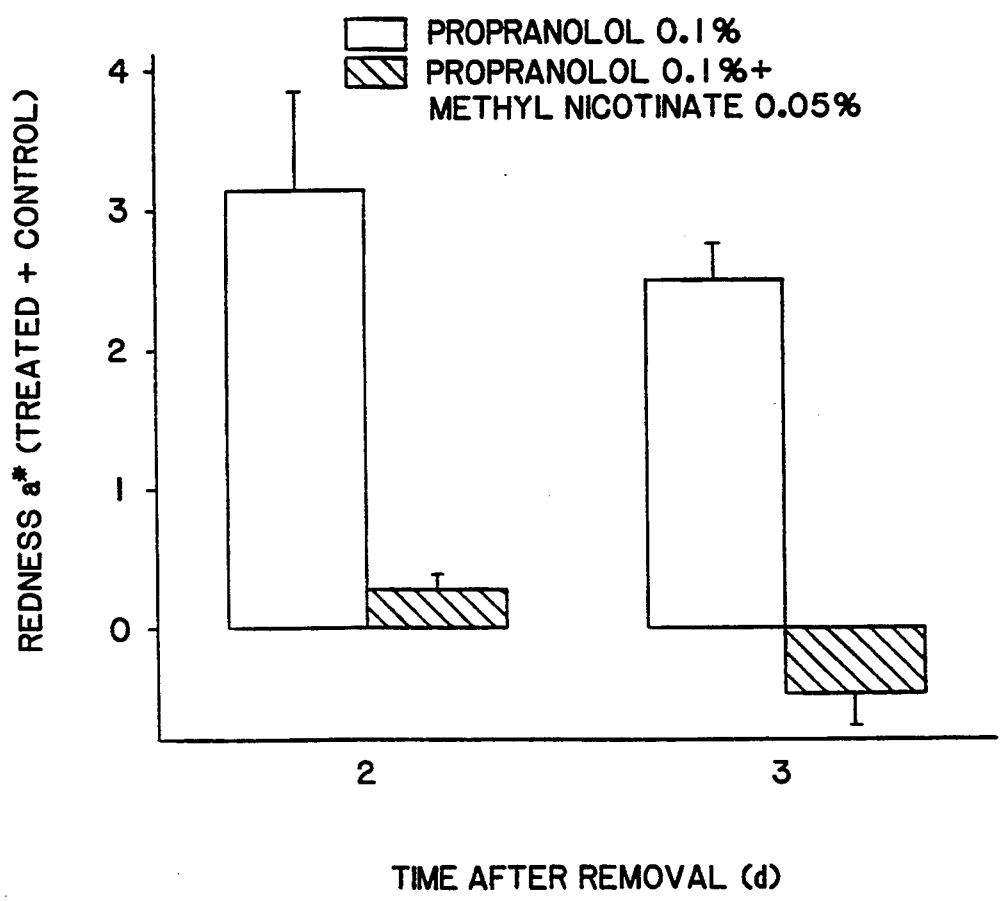
FIG. 6 is a graph showing the effect of methyl nicotinate on the elicitation of sensitization to propranolol.

0.020 ml of each formulation was placed in a Finn ® chamber. The chambers were applied to four sites on the upper arm of an adult male, who was known to be sensitized to propranolol. After two hours the chambers were removed and the sites washed. The intensity of the reaction was recorded two and three days later using the mean a* measurement recorded by a Minolta ® Chroma Meter. As can been in FIG. 6, methyl nicotinate inhibited the elicitation of the sensitization reaction.

EXAMPLE 3

The following formulations were made to determine the effect of methyl nicotinate on the elicitation of sensitization to ketoprofen:

1) 2 w/v percent ketoprofen, 32 w/v percent ethanol, 1.2 w/v percent acetic acid, 2 w/v percent hydroxyethylcellulose, NaOH q.s. pH 5 and distilled water q.s.,
2) 2 w/v percent ketoprofen, 0.1 w/v percent methyl nicotinate, 32 w/v percent ethanol, 1.2 w/v percent acetic acid, 2 w/v percent hydroxyethylcellulose, NaOH q.s. pH 5 and distilled water q.s.,
3) 2 w/v percent ketoprofen, 1.0 w/v percent methyl nicotinate, 32 w/v percent ethanol, 1.2 w/v percent acetic acid, 2 w/v percent hydroxyethylcellulose, NaOH q.s. pH 5 and distilled water q.s., and
4) 32 w/v percent ethanol, 1.2 w/v percent acetic acid, 2 w/v percent hydroxyethylcellulose, NaOH q.s. pH 5 and distilled water q.s.

0.1 ml of each formulation was placed in a Finn ® chamber, and applied to the backs of 10 hairless guinea pigs (Charles River). After 24 hours the cups were removed. The intensity of the reaction was scored visually on a random, blind basis according to the following scale:

TABLE 1

| | | Value |
|---|---|---|
| 1. | Erythema and Eschar Formation | |
| | No erythema | 0 |
| | Very slight erythema (barely perceptible) | 1 |
| | Well define erythema | 2 |
| | Moderate to severe erythema | 3 |
| | Severe erythema (beet redness) to slight eschar formation (injuries in depth) | 4 |
| 2. | Edema Formation | |
| | No edema | 0 |
| | Very slight edema (barely perceptible) | 1 |
| | Slight edema (edges of area well defined by definite raising) | 2 |
| | Moderate edema (raised approximately 1 mm) | 3 |
| | Severe edema (raised more than 1 mm and extending beyond the area of exposure) | 4 |
| | Total possible score | 8 |

Figure 7:
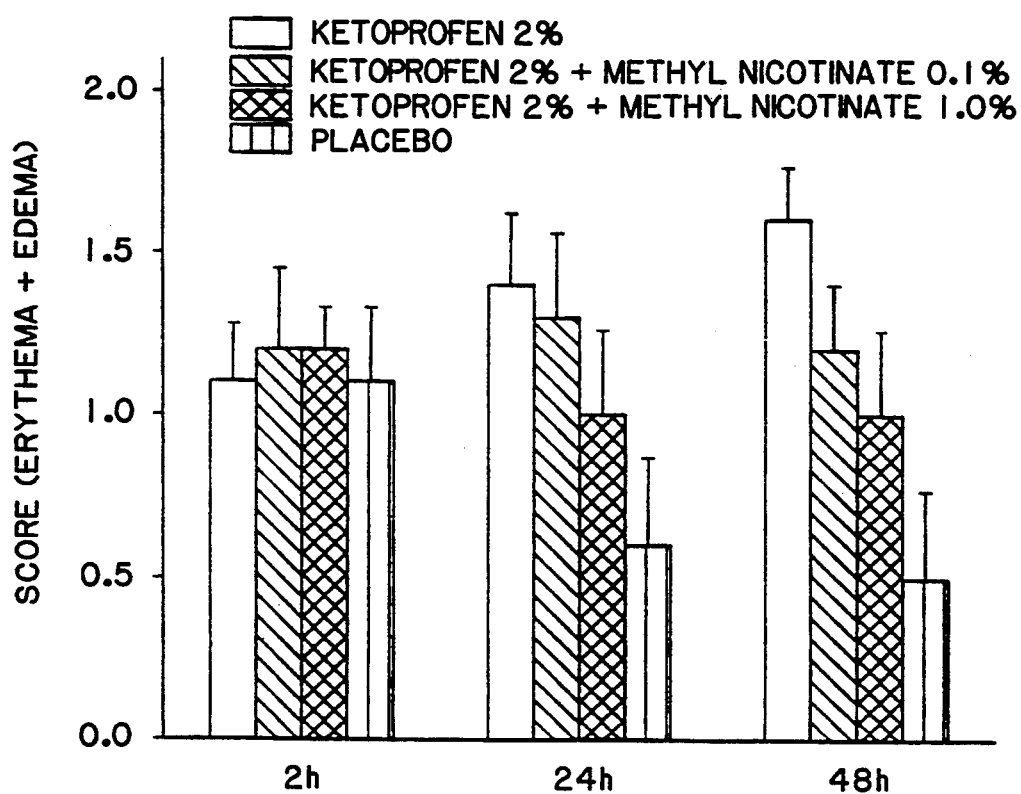
FIG. 7 is a graph showing the effect of methyl nicotinate on the elicitation of sensitization to ketoprofen.

As call be seen from FIG. 7 the average visual score of erythema and edema was greater at 24 and 48 hours for the formulations that contained no methyl nicotinate.

EXAMPLE 4

The following formulations were made to determine the effect of methyl nicotinate on the elicitation of sensitization to ketoprofen:

1) 2 w/v percent ketoprofen, 32 w/v percent ethanol, 1.2 w/v percent acetic acid, 2 w/v percent hydroxyethylcellulose, NaOH q.s. pH 5 and distilled water q.s.,
2) 2 w/v percent ketoprofen, 0.1 w/v percent methyl nicotinate, 32 w/v percent ethanol, 1.2 w/v percent acetic acid, 2 w/v percent hydroxyethylcellulose, NaOH q.s. pH 5 and distilled water q.s.,
3) 2 w/v percent ketoprofen, 1.0 w/v percent methyl nicotinate, 32 w/v percent ethanol, 1.2 w/v percent acetic acid, 2 w/v percent hydroxyethylcellulose, NaOH q.s. pH 5 and distilled water q.s.,
4) 4 w/v percent ketoprofen, 32 w/v percent ethanol, 1.2 w/v percent acetic acid, 2 w/v percent hydroxyethylcellulose, NaOH q.s. pH 5 and distilled water q.s.,
5) 4 w/v percent ketoprofen, 0.1 w/v percent methyl nicotinate, 32 w/v percent ethanol, 1.2 w/v percent acetic acid, 2 w/v percent hydroxyethylcellulose, NaOH q.s. pH 5 and distilled water q.s.,
6) 4 w/v percent ketoprofen, 1.0 w/v percent methyl nicotinate, 32 w/v percent ethanol, 1.2 w/v percent acetic acid, 2 w/v percent hydroxyethylcellulose, NaOH q.s. pH 5 and distilled water q.s., and
7) 32 w/v percent ethanol, 1.2 w/v percent acetic acid, 2 w/v percent hydroxyethylcellulose, NaOH q.s. pH 5 and distilled water q.s.

Figure 8:
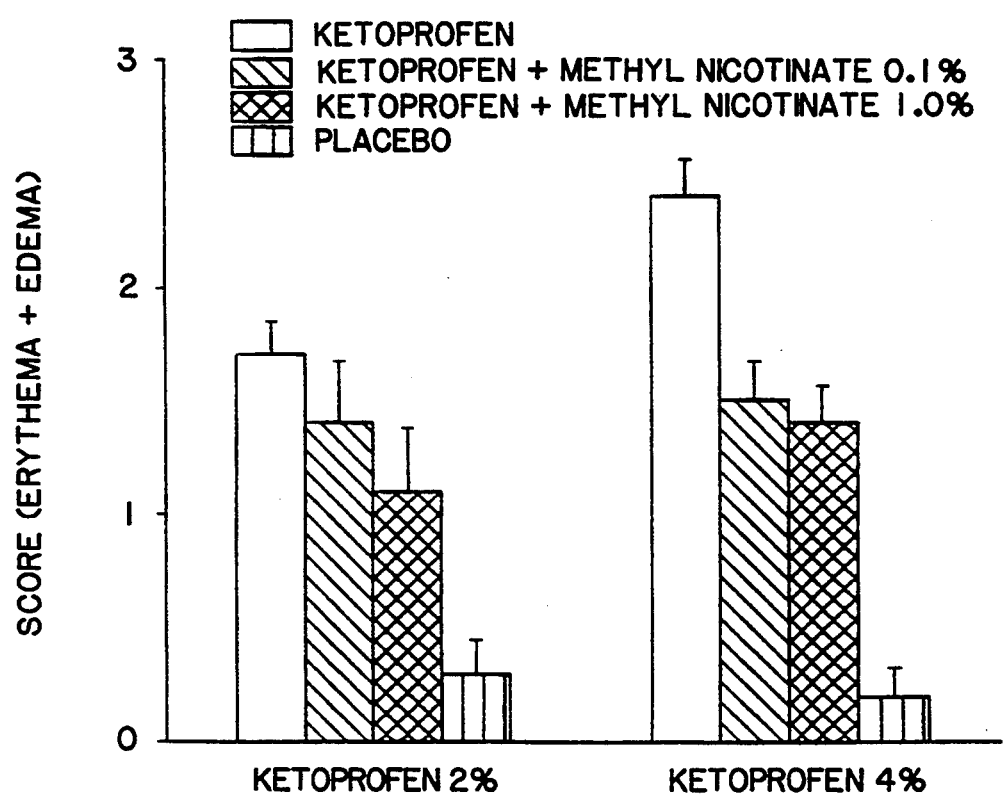
FIG. 8 is a graph showing the effect of methyl nicotinate on the elicitation of sensitization to ketoprofen.

0.1 ml of formulations 1, 2, 3 and 7 were placed in a Finn ® chamber, and applied to the backs of 10 hairless guinea pigs (Charles River) previously sensitized to ketoprofen. After 24 hours the cups were removed. The intensity of the reaction was scored visually 48 hours after removal on a random, blind basis according to the scale given in Table 1. After a rest period, this procedure was repeated on the same animals using formulations 4, 5, 6 and 7. As can be seen from FIG. 8, the average visual score of erythema and edema was greater for the formulations that contained no methyl nicotinate.

EXAMPLE 5

The following formulations were made to determine the effect of methyl nicotinate on the cumulative irritation produced by tetracaine HCl during the induction phase:

1) 2 w/v percent tetracaine HCl, 28 w/v percent ethanol, 5 w/v percent HEPPS, 2 w/v percent hydroxypropylcellulose, NaOH q.s. pH 8 and distilled water q.s.,
2) 2 w/v percent tetracaine HCl, 1.0 w/v percent methyl nicotinate, 28 w/v percent ethanol, 5 w/v percent HEPPS, 2 w/v percent hydroxypropylcellulose, NaOH q.s. pH 8 and distilled water q.s., and
3) 28 w/v percent ethanol, 5 w/v percent HEPPS, 2 w/v percent hydroxypropylcellulose, NaOH q.s. pH 8 and distilled water q.s.

0.1 ml of each formulation was placed in a Finn ® chamber, and applied to the back of a hairless guinea pigs (Charles River). After 6 hours the chambers were removed. This was repeated a total of nine times. The inductions were alternated between two sites, such that one site received five applications and the other site received four applications. Two, 24 and 48 hours after removal of the first, fourth, seventh and ninth applications, the treatment sites were scored to assess irritation. The results appear in Table 2. The intensity of the reaction was scored visually on a random, blind basis according to the scale given in Table 1. The results are given in Table 2.

TABLE 2

| | Application | | | | | | | | | | | |
|---|---|---|---|---|---|---|---|---|---|---|---|---|
| | One | | | Four | | | Seven | | | Nine | | |
| Formulation | 2 h | 24 h | 48 h | 2 h | 24 h | 48 h | 2 h | 24 h | 48 h | 2 h | 24 h | 48 h |
| 2% tetracaine | 1.9 | 1.2 | 1.1 | 2.7 | 2.6 | 1.8 | 5.8 | 5.9 | 5.6 | 6.7 | 6.6 | 6.0 |
| 2% tetracaine + 1% methyl | 2.3 | 1.3 | 0.5 | 2.3 | 2.2 | 1.0 | 5.8 | 5.7 | 5.3 | 6.1 | 6.3 | 6.0 |

TABLE 2-continued

| | Application | | | | | | | | | | | |
|---|---|---|---|---|---|---|---|---|---|---|---|---|
| | One | | | Four | | | Seven | | | Nine | | |
| Formulation | 2 h | 24 h | 48 h | 2 h | 24 h | 48 h | 2 h | 24 h | 48 h | 2 h | 24 h | 48 h |
| nicotinate | | | | | | | | | | | | |
| Control | 0.8 | 0.5 | 0.1 | 0.2 | 0.2 | 0.0 | 0.2 | 0.2 | 0.2 | 0.3 | 0.1 | 0.0 |

After the ninth induction exposure, the animals received no treatment for two weeks. The following formulations were used to determine the effect of methyl nicotinate on the sensitization and elicitation of sensitization to tetracaine during the challenge phase:

1) 1 w/v percent tetracaine HCl, 28 w/v percent ethanol, 5 w/v percent HEPPS, 2 w/v percent hydroxypropylcellulose, NaOH q.s. pH 8 and distilled water q.s.,
2) 1 w/v percent tetracaine HCl, 1.0 w/v percent methyl nicotinate, 28 w/v percent ethanol, 5 w/v percent HEPPS, 2 w/v percent hydroxypropylcellulose, NaOH q.s. pH 8 and distilled water q.s., and
3) 28 w/v percent ethanol, 5 w/v percent HEPPS, 2 w/v percent hydroxypropylcellulose, NaOH q.s. pH 8 and distilled water q.s.

0.1 ml of each formulation was placed in a Finn® chamber. The chamber was then applied to the backs of the animals for 6 hours on previously untreated sites. Treatment sites were visually scored two, 24, 48, and 72 hours after removal using the scale given in Table 1. The results are given in Table 3.

TABLE 3

| | Application | | | | | | | | | | | |
|---|---|---|---|---|---|---|---|---|---|---|---|---|
| | 2% tetracaine | | | | 2% tetracaine + 1% methyl nicotinate | | | | Control | | | |
| Formulation | 2 h | 24 h | 48 h | 72 h | 2 h | 24 h | 48 h | 72 h | 2 h | 24 h | 48 h | 72 h |
| 1% tetracaine | 3.4 | 2.5 | 2.2 | 2.1 | 2.8 | 2.3 | 2.1 | 2.0 | 1.6 | 1.0 | 0.8 | 0.6 |
| 1% tetracaine + methyl nicotinate | 3.4 | 2.4 | 2.0 | 2.0 | 3.2 | 2.3 | 2.1 | 2.0 | 1.7 | 1.0 | 0.9 | 0.6 |
| Control | 1.0 | 0.1 | 0.5 | 0.4 | 0.2 | 0.2 | 0.2 | 0.0 | 0.8 | 0.1 | 0.1 | 0.0 |

At the 72 hour reading, it was realized the visual rating system did not have a sufficient level of sensitivity. The test sites of the animals were then scored using a Minolta® Chroma Meter. The results appear in Table 4.

TABLE 4

| | Induction Formulation | | |
|---|---|---|---|
| Challenge Formulation | 2% tetracaine 72 h a" value | 2% tetracaine + 1% methyl nicotinate 72 h a" value | Control 72 h a" value |
| 1% tetracaine | 12.8 | 10.6 | 8.8 |
| 1% tetracaine + 1% methyl nicotinate | 11.5 | 11.0 | 8.9 |
| Control | 8.8 | 9.1 | 9.5 |

Figure 9:
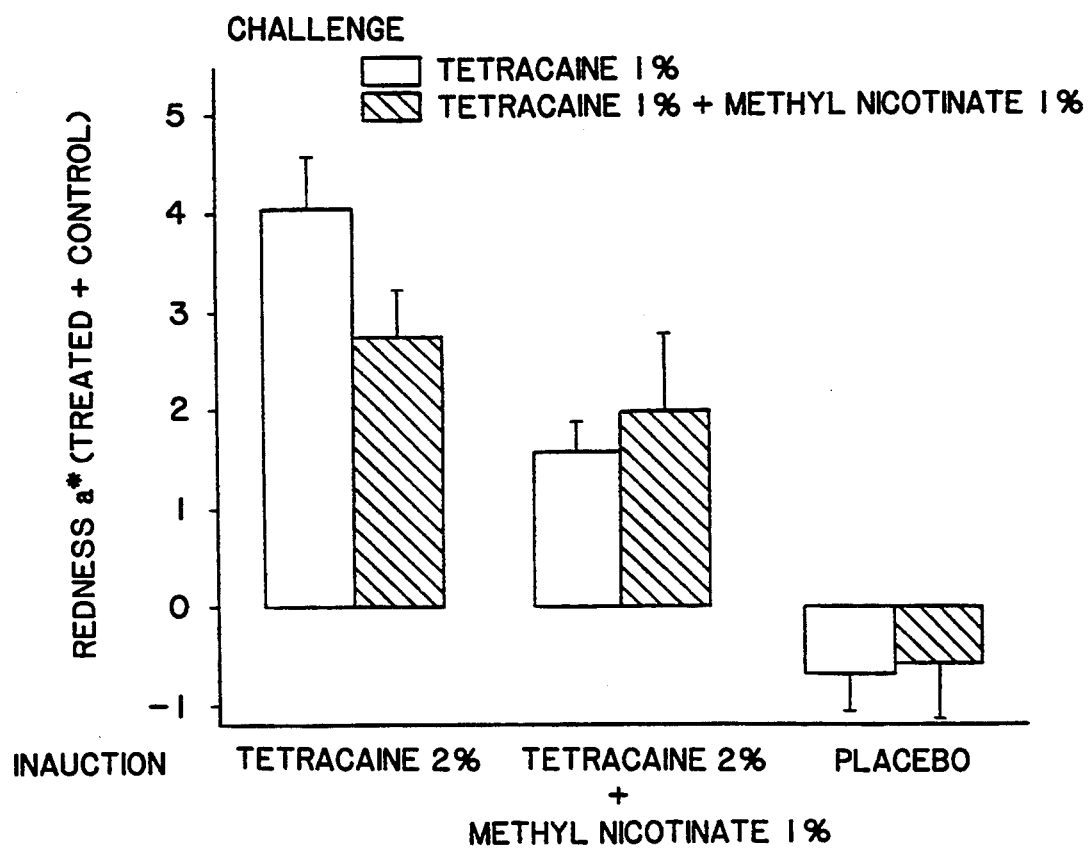
FIG. 9 is a graph showing the effect of methyl nicotinate on the sensitization and elicitation reactions to tetracaine.

The Minolta® scores indicate that methyl nicotinate decreased both the sensitization and elicitation reactions as can be seen in FIG. 9.

Having thus generally described the present invention and described certain specific embodiments thereof including the embodiments that the applicants consider the best mode of practicing their invention, it will be readily apparent that various modifications to the invention may be made by workers skilled in the art without departing from the scope of this invention which is limited only by the following claims.

What is claimed is:

1. A device for the transdermal coadministration of methyl nicotinate and a drug used for systemic therapy, which drug, following transdermal administration produces skin irritation in an animal, including a human, which device comprises:
   (a) a reservoir comprising the irritating drug and methyl nicotinate, wherein the drug is present in an amount sufficient is to be delivered to the skin at a systemically therapeutically effective rate, and wherein the methyl nicotinate is present in the amount sufficient to be delivered to the systemic circulation through said area of skin at a irritation reducing rate; and
   (b) a means for maintaining the reservoir in drug- and methyl nicotinate-transmitting relation with the skin.

2. A device for the transdermal coadministration of methyl nicotinate and a drug used for systemic therapy, which drug, following transdermal administration, produces sensitization in an animal, including a human, which device comprises:
   (a) a reservoir comprising the sensitizing drug and methyl nicotinate, wherein the drug is present in an amount sufficient to be delivered to the skin at a systemically therapeutically effective rate, and wherein the methyl nicotinate is present in an amount sufficient to be delivered to the systemic circulation through said area of skin at a sensitization reducing rate; and
   (b) a means for maintaining the reservoir in drug- and methyl nicotinate-transmitting relation with the skin.

3. A device according to claim 1 or 2, wherein the means for maintaining the reservoir in relation with the skin comprises an inline adhesive layer on the skin-proximal surface of the reservoir.

4. A device according to claim 1 or 2, further comprising a rate controlling membrane.

5. A device according to claim 1 or 2, wherein the reservoir further comprises a permeation enhancer.

6. A device according to claim 1 or 2, wherein the methyl nicotinate is present in the reservoir in an amount of 0.005 to 10.0 percent w/v.

7. A method for reducing irritation or sensitization during transdermal delivery to an animal, including a human, caused by systemic transdermal delivery of an irritating or sensitizing drug, the method comprising the step of placing a transdermal delivery device for delivery, onto the skin of an animal, the device comprising:

(a) a reservoir comprising a systemically therapeutically effective amount of an irritating or sensitizing drug and methyl nicotinate in a skin irritation or sensitization reducing-amount;

(b) a backing on the skin-distal surface of the reservoir; and (c) means for maintaining the reservoir in drug- and methyl nicotinate-transmitting relation with the skin.

8. A method according to claim 7, wherein the methyl nicotinate is present in the reservoir in an amount of 0.005 to 10.0 percent w/v.

9. A method according to claim 7 wherein the means for maintaining the reservoir in relation with the skin comprises an in-line adhesive layer on the skin-proximal surface of the reservoir.

10. A method according to claim 7, wherein the reservoir further comprises a permeation enhancer.

* * * * *